United States Patent
Wang et al.

(10) Patent No.: US 9,488,632 B2
(45) Date of Patent: Nov. 8, 2016

(54) REHEATING COOKED FOOD SUCH AS MEAT

(71) Applicant: KONINKLIJKE PHILIPS N.V., Eindhoven (NL)

(72) Inventors: Gang Wang, Eindhoven (NL); Yun Chen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/909,291

(22) PCT Filed: Jul. 28, 2014

(86) PCT No.: PCT/IB2014/063471
§ 371 (c)(1),
(2) Date: Feb. 1, 2016

(87) PCT Pub. No.: WO2015/019236
PCT Pub. Date: Feb. 12, 2015

(65) Prior Publication Data
US 2016/0178591 A1    Jun. 23, 2016

(30) Foreign Application Priority Data

Aug. 6, 2013   (WO) ................ PCT/CN2013/000917
Sep. 2, 2013   (EP) ..................................... 13182549

(51) Int. Cl.
*G01N 33/12* (2006.01)
*H05B 6/64* (2006.01)
(Continued)

(52) U.S. Cl.
CPC ............ *G01N 33/12* (2013.01); *A23L 1/0128* (2013.01); *A23L 1/31* (2013.01); *G01N 21/27* (2013.01);
(Continued)

(58) Field of Classification Search
CPC ............... G01N 33/12; G01N 21/314; G01N 21/3563; G01N 21/27; G01N 21/3151; G01N 21/3155; G01N 2201/061; A23L 1/0128; A23L 1/31; H05B 6/687; H05B 6/664; H05B 6/6467; A23V 2002/00
See application file for complete search history.

(56) References Cited

U.S. PATENT DOCUMENTS 3,890,825 A   6/1975  Davis
4,310,763 A   1/1982  Shields
(Continued)

FOREIGN PATENT DOCUMENTS

EP   1504665 A1   2/2005
EP   1677578 A1   7/2006
WO   2011050486 A1   5/2011

*Primary Examiner* — Steven Leff (57) ABSTRACT

In order to provide reheating of cooked food that leads to an improved result of the reheated food, e.g. meat, in a facilitated manner, an apparatus (10) for reheating cooked food is provided that comprises a container (12) for receiving food to be reheated, a sensing module (16), a heating module (18), and a processing unit (20). The sensing module is provided with an emitter arrangement (22) configured to emit at least light as first sensing radiation ($SRA_1$) with a first sensing peak wavelength ($SWL_1$), and light as second sensing radiation ($SRA_2$) with a second sensing peak wavelength ($SWL_2$). The first and the second sensing radiations have different reflecting characteristics in relation with fat and protein in the food, e.g. meat to be reheated. The sensing module is also provided with a sensor arrangement (24) configured to detect light with the first sensing peak wavelength and light with the second sensing peak wavelength; wherein the light is reflected by the food. The heating module is configured to provide energy to the food arranged in the container by at least one heating radiation source (30) for heating the food in dependency of a determined fat/protein ratio. The processing unit is configured to determine the fat/protein ratio (32) of the food arranged in the container based on the detected light reflected by the food. The processing unit is configured to determine operating parameters (38) of the heating module, and to control the heating radiation source to emit light as first heating radiation ($HRA_1$) with a first heating peak wavelength ($HWL_1$), and light as second heating radiation ($HRA_2$) with a second heating peak wavelength ($HWL_2$). A power output of the first heating peak wavelength and the second heating peak wavelength is adapted to have a different absorption characteristics relating to fat and protein of the food/meat.

15 Claims, 6 Drawing Sheets

(51) Int. Cl.
    *A23L 1/01*     (2006.01)
    *G01N 21/31*     (2006.01)
    *A23L 1/31*     (2006.01)
    *G01N 21/27*     (2006.01)
    *G01N 21/3563*     (2014.01)
    *H05B 6/66*     (2006.01)
    *H05B 6/68*     (2006.01)

(52) U.S. Cl.
    CPC ........ *G01N 21/314* (2013.01); *G01N 21/3563* (2013.01); *H05B 6/6467* (2013.01); *H05B 6/664* (2013.01); *H05B 6/687* (2013.01); *A23V 2002/00* (2013.01); *G01N 21/3151* (2013.01); *G01N 2021/3155* (2013.01); *G01N 2201/061* (2013.01)

(56) References Cited

U.S. PATENT DOCUMENTS

| | | |
|---|---|---|
| 4,415,809 A | 11/1983 | Shields |
| 5,247,460 A | 9/1993 | LaBudde |
| 5,472,721 A | 12/1995 | Eisenberg |

REHEATING COOKED FOOD SUCH AS MEAT

This application is the U.S. National Phase application under 35 U.S.C. §371 of International Application No. PCT/IB2014/063471, filed on Jul. 28, 2014, which claims the benefit of International Application No. 13182549.9 filed on Sep. 2, 2013 and International Application No. PCT/CN2013/000917 filed on Aug. 6, 2013. These applications are hereby incorporated by reference herein.

FIELD OF THE INVENTION

The present invention refers to reheating cooked food, in particular cooked meat, and relates to an apparatus for reheating cooked food, and to a method for reheating cooked food.

BACKGROUND OF THE INVENTION

After the preparation and cooking of food, it may become necessary to reheat the food, for example in case of leftovers of a meal that are then consumed at a further meal. Another reason may be a difference between the eating schedule among different persons living in a common household. For reheating food, the food may be placed in a pan or, more convenient, in a microwave oven. Another possibility for reheating food is to put the dish into an oven and to apply radiation and also a circulating hot air flow. A further possibility is to provide infrared radiation. For example, U.S. Pat. No. 5,472,721 describes a method of grilling and heating a food product, where an infrared heater is electrically operated in a discontinuous manner between a first supply level during a first time and a second supply level during a second time in order to generate infrared radiation and to heat the product thereby. In particular in relation to reheating cooked meat, for example braised pork or others, the quality of the dish, relating to taste as well as to texture, is a major topic that requires attention. Thus, as a result, the reheating procedure may lead to a decrease in taste and texture qualities. However, it has been shown that the reheating procedure needs adaption relating to the individual consistency of the food that is to be reheated.

SUMMARY OF THE INVENTION

There may be a need to provide reheating of cooked food that leads to an improved result of the reheated food, e.g. meat, in a facilitated manner.

The object of the present invention is solved by the subject-matter of the independent claims, wherein further embodiments are incorporated in the dependent claims. It should be noted that the following described aspects of the invention apply also for the apparatus for reheating cooked food and the method for reheating cooked food.

According to the present invention, an apparatus for reheating cooked food is provided that comprises a container for receiving food to be reheated. The apparatus further comprises a sensing module, a heating module, and a processing unit. The sensing module is provided with an emitter arrangement configured to emit at least light as first sensing radiation with a first sensing peak wavelength, and light as second sensing radiation with a second sensing peak wavelength. The first and the second sensing radiations have different reflecting characteristics in relation with fat and protein in the food to be reheated. The sensing module is further provided with a sensor arrangement configured to detect light with the first sensing peak wavelength and light with the second sensing peak wavelength. The light is reflected by the food. The heating module is configured to provide energy to the food arranged in a container by at least one heating radiation source for heating the food in dependency of a determined fat/protein ratio. The processing unit is configured to determine a fat/protein ratio of the food arranged in the container based on the detected light reflected by the food. The processing unit is further configured to determine operating parameters of the heating module. The processing unit is still further configured to control the heating radiation source to emit light as first heating radiation with a first heating peak wavelength, and light as second heating radiation with a second heating peak wavelength. A power output of the first heating peak wavelength and the second heating peak wavelength are adapted to have a different absorption characteristics relating to fat and protein of the food.

In an example, the food to be reheated is meat.

As an advantage, the apparatus for reheating cooked food is capable of determining a current characteristic of meat that is about to be reheated. For this reason, the fat/protein ratio is determined with the application of two different types of light, i.e. two different wavelengths, that each have different reflecting characteristics when applied to fat or protein. Thus, the reflected light gives an indication about the current food substance, e.g. meat substance, and its properties relating to the two main components fat and protein. Further, the application of heating radiation is then adapted to the determined fat/protein ratio. Thus, the heating radiation is adjusted to the individual situation, i.e. to the particular food/meat that is to be reheated. Hence, an optimum result can be achieved, since it is possible to apply the heating radiation such that the different ingredients/substances of the food/meat can be perfectly addressed.

The term "heating radiation source" relates to a source that provides the heat to the food, e.g. meat via radiation. For example, the radiation is light radiation, e.g. in the invisible light range. In an example, the heating radiation source is a heating light source.

The term "determined fat/protein ratio" relates to a fat/protein ratio that is determined based on the detected light reflected by the food. Hence, the fat/protein ratio is an estimated fat/protein ratio that may show at least a small deviation from the actual fat/protein ratio of the food. Since the determined fat/protein ratio is based on the detected, i.e. measured reflected light (light measured by the sensor arrangement), the determined fat/protein ratio could also be referred to as measured fat/protein ratio.

In an example, the two sensing radiations are applied as visible sensing radiations.

According to an example, the processing unit is configured to determine operating parameters of the heating module for a reheating procedure such that fat parts and protein parts are equally heated. The reheating procedure may also be referred to as optimal reheating procedure.

According to an example, the visible wavelength of the first visible sensing radiation is approximately 550 nm (nanometers), and the second visible wavelength of the second visible sensing radiation is approximately 780 nm.

In a further example, the sensing radiation is provided as infrared sensing radiation.

According to an example, the first infrared wavelength of the first infrared sensing radiation is approximately 1200 nm, and the second infrared wavelength of the second infrared sensing radiation is approximately 1300 nm.

In a further example, a combination of visible and infrared sensing radiation is provided.

In a still further example, in addition to two sensing radiations, a third sensing radiation is provided as further redundancy.

In a still further example, in addition to two sensing radiations, two separate sensing radiations are provided for an additional possibility for determining a fat/protein ratio.

According to an example, a first and a second heating peak wavelengths are provided in the infrared wavelength range. The first heating peak wavelength is approximately 1200 nm, and the second heating peak wavelength is approximately 1600 nm.

According to the present invention, also a method for reheating cooked food is provided, comprising the following steps:
a) arranging cooked food to be reheated in a container;
b) emitting radiation to the food; wherein it is provided:
   b1) emitting a first sensing radiation with a first sensing peak wavelength, and
   b2) emitting a second sensing radiation with a second sensing peak wavelength; wherein the first and the second sensing radiations have different reflecting characteristics in relation with fat and protein in the food to be reheated;
c) detecting light reflected by the food; wherein it is provided:
   c1) detecting light with the first sensing peak wavelength; and
   c2) detecting light with the second sensing peak wavelength;
d) determining a fat/protein ratio of the food arranged in the container based on the light detected in sub-steps c1) and c2);
e) determining operating parameters for a heating module; and
f) controlling the heating radiation source such that light as first heating radiation with a first heating peak wavelength and light as second heating radiation with a second heating peak wavelength is emitted to the food in the container, thereby reheating the cooked food; wherein a power output of the first heating peak wavelength and the second heating peak wavelength is adapted to have a different absorption characteristics relating to fat and protein of the food.

In an example, the operating parameters for the heating module are determined for an optimal reheating procedure in step e).

In an example, the power output and/or the duty cycle of the first heating radiation and the second heating radiation is adapted. For example, in case of two heat sources, the power output and/or the duty cycle of the two heat sources is adapted.

In an example, the heating peak wavelengths are fixed, for example 1200 nm and 1600 nm, and the power output and/or duty cycle is adapted.

According to an aspect, the power output of, for example, two infrared heaters is adjusted to match an estimated fat/protein ratio so as to deliver a better heating result. Thus, it is provided to apply energy to heat the protein and energy to heat the fat in a separate way, in order to adjust the heat application for improving the quality of the reheated food. The fat/protein ratio is determined by the application of two different wavelengths, based on different reflecting characteristics of the protein and the fat. These two substances are, besides water, the main components in cooked meat, at least with respect to the reheating procedure. It is thus avoided to overheat fat, which could otherwise burst or even worse becomes burnt, which would seriously affect the food texture and taste. By determining the fraction of incident light which is reflected by the cooked meat, it is possible to determine the ratio of fat and protein in the meat. For this purpose, two different wavelengths are used, which can either be in the visible range, for example between 500 nm and 800 nm, e.g. 550 nm and 780 nm, or in the infrared spectrum, for example between 1200 nm and 1300 nm. The result is then used for the application of infrared light for heating purposes. For example, for heating meat which mainly contains protein, only an infrared heater with peak wavelength at 1600 nm is turned on, and for heating meat which mainly contains fat, only an infrared heater with peak wavelength at 1200 nm is turned on. The duty cycle of the two heaters is adjusted according to the fat/protein ratio.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
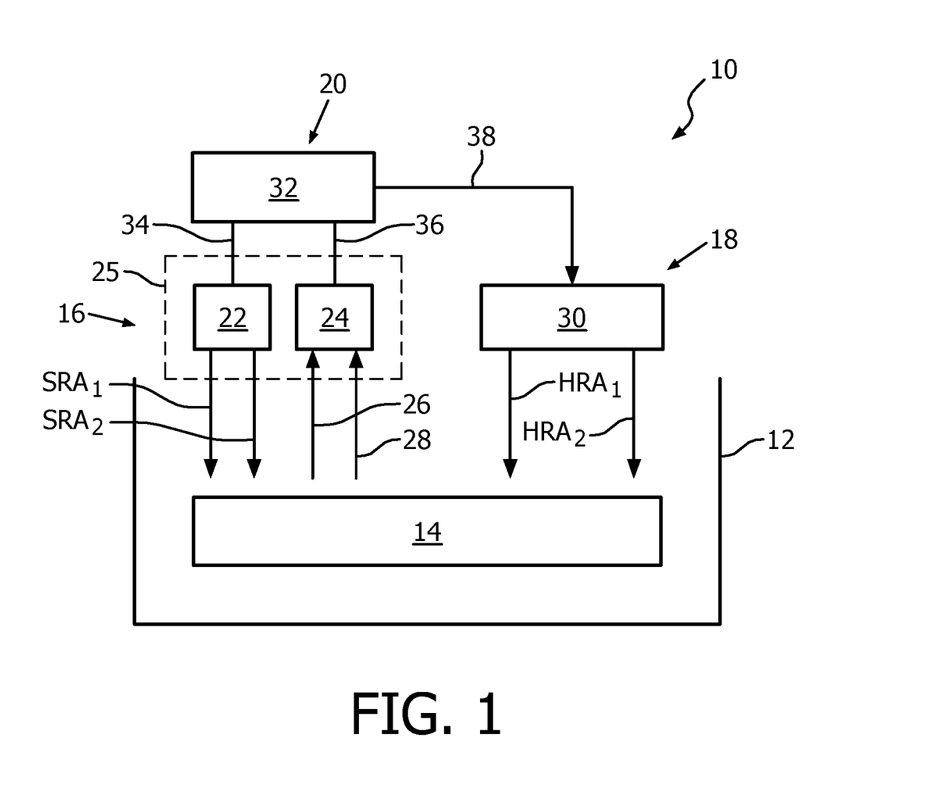
FIG. 1 shows a schematic cross-section through an apparatus for reheating cooked food with a first example of a sensing module and a heating module.

FIG. 1 shows an apparatus 10 for reheating cooked food. The apparatus comprises a container 12 for receiving food 14 to be reheated. The food 14 is symbolically indicated by a frame. The food relates in particular to meat that is to be reheated. Further, a sensing module 16 is provided, and a heating module 18. Still further, a processing unit 20 is provided. The processing unit 20 is connected to the sensing module 16 and the heating module 18. The sensing module 16 is provided with an emitter arrangement 22 configured to emit at least light as first sensing radiation $SRA_1$ with a first sensing peak wavelength $SWL_1$. The sensing module 16 is further configured to emit light as second sensing radiation $SRA_2$ with a second sensing peak wavelength $SWL_2$. The first and the second sensing radiations have different reflecting characteristics in relation with fat and protein in the food/meat to be reheated.

The sensing module 16 is further provided with a sensor arrangement 24 configured to detect light with the first sensing peak wavelength, indicated with arrow 26, and light with the second sensing peak wavelength, indicated with a further arrow 28. The light, i.e. the two sensing peak wavelengths, is reflected by the food 14.

A frame 25 indicates the possibility to provide the emitter arrangement 22 and the sensor arrangement 24 in an integrated or combined manner.

The heating module 18 is configured to provide energy to the food 14 arranged in the container 12 by at least one heating radiation source 30 for heating the food in dependency of a determined fat/protein ratio.

The processing unit 20 is configured to determine a fat/protein ratio 32 of the food arranged in the container based on the detected light reflected by the food. For this purpose, the sensing module 16 provides the respective data to the processing unit 20, as indicated with first and second data connection lines 34, 36. The processing unit 20 is configured to determine operating parameters 38 of the heating module 18, e.g. for an optimal reheating procedure. The operating parameters 38 are supplied, as indicated with an arrow at 38 to the heating module 18. The processing unit 20 is configured to control the heating radiation source 30 to emit light as first heating radiation $HRA_1$ with a first heating peak wavelength $HWL_1$, and light as second heating radiation $HRA_2$ with a second heating peak wavelength $HWL_2$. A power output of the first heating peak wavelength and the second heating peak wavelength is adapted to have a different absorption characteristics relating to fat and protein of the food.

For example, the container provides a volume for receiving cooked food that is to be reheated.

The term "optimal reheating procedure" relates to a way of heating the food such that fat parts and protein parts are approximately equally heated, e.g. equally heated. In an example, the optimal reheating procedure is provided according to predetermined criteria. The term "predetermined criteria" relates to the option of adjusting the balance of the heating fat and protein according to personal taste, as well as to cultural and religious aspects, at least within a limited range.

According to a further example, the emitter arrangement 22 is configured to emit the first sensing radiation as a first visible sensing radiation $SRA_{VIS1}$ with a first visible wavelength $SWL_{VIS1}$, and the second sensing radiation as a second visible sensing radiation $SRA_{VIS2}$ with a second visible wavelength $SWL_{VIS2}$. For this reason, the sensor arrangement 24 comprises a first visible light sensor 40 to detect light with the first visible wavelength, and a second visible light sensor 42 to detect light with the second visible wavelength.

Figure 2A:
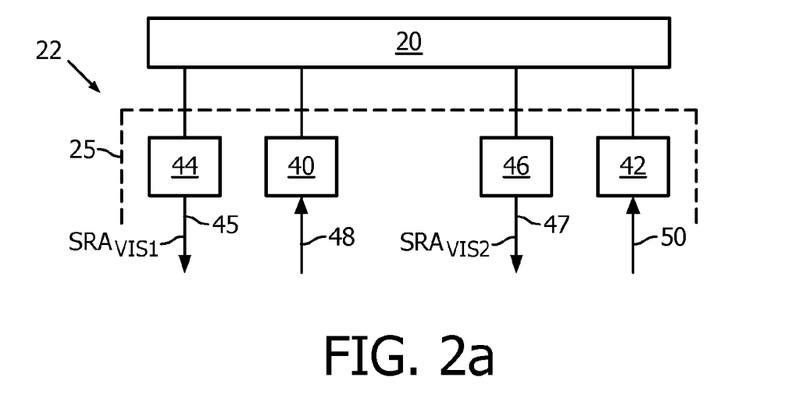
FIG. 2A shows a schematic section of a first example of a sensing module with visible sensing radiation.

As can be seen in a first example in FIG. 2A, a first visible light emitter 44 and a second visible light emitter 46 are provided. The first visible light emitter 44 is providing a first spectrum 45 comprising the first visible wavelength, and the second visible light emitter 46 is providing a second spectrum 47 comprising the second visible wavelength. An arrow 48 indicates the reflected light with the first visible wavelength and a further arrow 50 indicates the reflected light with the second visible wavelength.

Figure 2B:
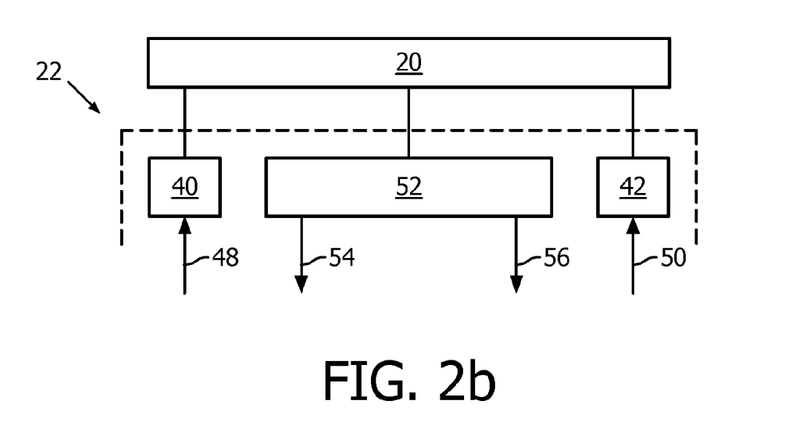
FIG. 2B shows a second example of a sensing module.

FIG. 2B shows a further example, where the emitter arrangement 22 is provided with a wide-spectrum-emitter 52 providing a wide spectrum radiation comprising the first visible wavelength, as indicated with arrow 54, and the second visible wavelength, as indicated with arrow 56.

In an example, the wide-spectrum-emitter is also referred to as a dual peak emitter providing a dual radiation spectrum comprising the first visible wavelength and the second visible wavelength.

Figure 2C:
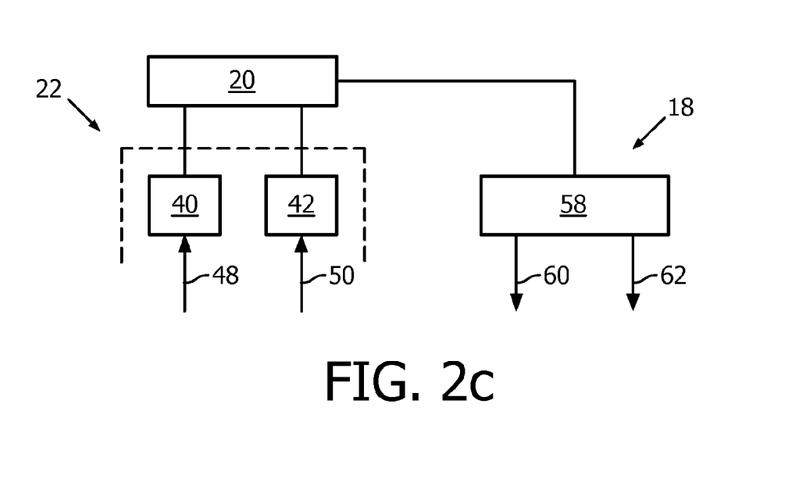
FIG. 2C shows a third example.

FIG. 2C shows a third example, wherein, as the emitter arrangement 22, one of the at least one heating radiation sources is provided as a bi-functional light source $LS_{BI-F}$, indicated with reference numeral 58, configured to emit light for measuring purposes with a wide spectrum radiation comprising the first visible wavelength, as indicated with arrow 60, and the second visible wavelength, as indicated with arrow 62.

In an example, the bi-functional light source is configured to emit light for measuring purposes with a dual radiation spectrum comprising the first visible wavelength and the second visible wavelength.

It must be noted that in case of FIG. 2C, the term "emitter arrangement" comprises the function of the emitting of the respective sensing radiation, which is provided in an integrated manner due to different functions provided by the heat source itself. In other words, the heating module 18 also provides the function of the emission of radiation, which is part of the sensing module.

It must be noted that the emitter solutions of FIGS. 2A, 2B, and 2C are provided as alternative options.

In an example, not further shown, the first and second visible light sensors are provided as photodiodes.

Instead of two separate sensors, also an integrated sensor, or dual sensor, is provided configured to detect light with the first and the second peak wavelength.

The wide spectrum radiation, or dual radiation spectrum, of FIGS. 2B and 2C comprises the first sensing radiation $SRA_1$ with the first sensing peak wavelength $SWL_1$, and the second sensing radiation $SRA_2$ with the second sensing peak wavelength $SWL_2$.

In another example, as the emitter arrangement, one of the at least one heating radiation sources is provided as a bi-functional light source $LS_{BI-F}$, configured to emit light for measuring purposes with a wide spectrum radiation, or dual radiation spectrum, comprises the first visible wavelength or the second visible wavelength. For the respective other second or first visible wavelength, an emitter is provided.

It must be noted that in the context of the present invention, the term "approximately" relates to a range comprising a deviation of maximum ±25%, e. g. maximum ±10%, e. g. ±5%.

In a further example, the emitter arrangement is configured to emit the first sensing radiation $SRA_1$ as first infrared sensing radiation $SRA_{IR1}$ with a first infrared wavelength $SWL_{IR1}$, and the second sensing radiation $SRA_2$ as a second infrared sensing radiation $SRA_{IR2}$ with a second infrared wavelength $SWL_{IR2}$.

The sensor arrangement 24 comprises an infrared sensor device 63 to detect light with a first infrared wavelength, as indicated with arrow 65, and to detect light with the second infrared wavelength, as indicated with arrow 67.

Figure 3A:
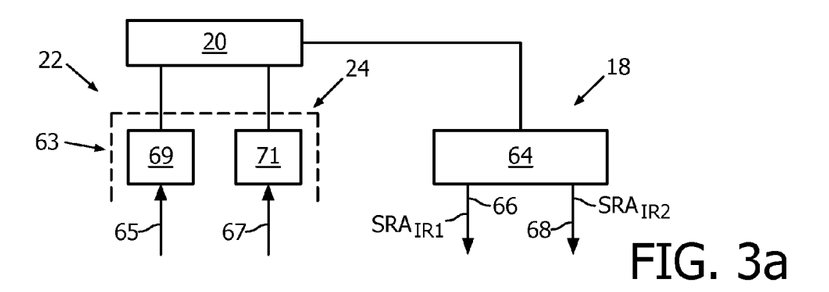
FIG. 3A shows a first example of a further example of a sensing module with infrared sensing radiation.

FIG. 3A shows an example, wherein, as the emitter arrangement 22, one of the at least one heating radiation sources is provided as a bi-functional light source $LS_{BI-F}$, indicated with reference numeral 64, configured to emit light for measuring purposes with a wide spectrum radiation, comprising the first infrared wavelength, as indicated with arrow 66, and the second infrared wavelength, as indicated with arrow 68.

For example, the infrared sensor device 63 comprises a first infrared sensor 69 to detect light with the first infrared wavelength, and a second infrared sensor 71 to detect light with the second infrared wavelength.

Figure 3B:
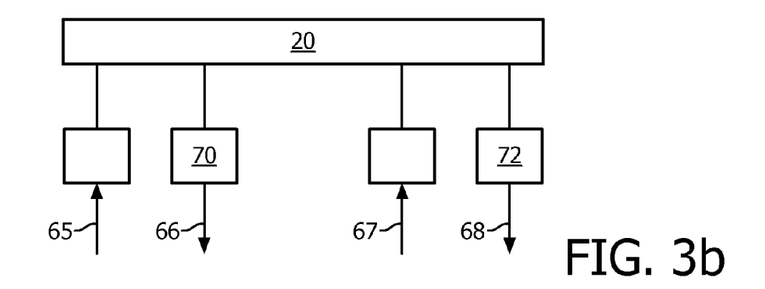
FIG. 3B shows a second example.
Figure 3C:
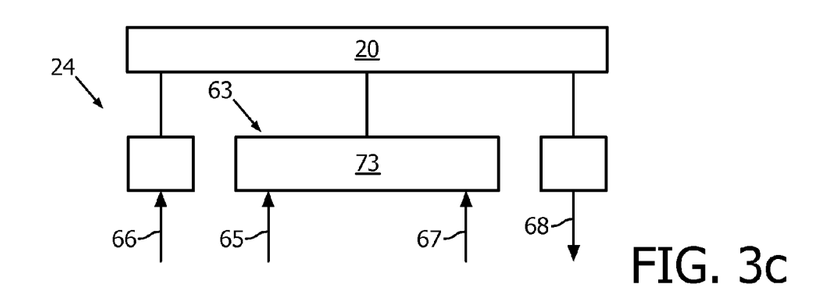
FIG. 3C shows a third example.

Instead of the first and the second infrared sensors 69, 71, it is further provided a wide-responsive infrared sensor 73, as shown in FIG. 3C, with a plateau-shaped responsive curve covering the first infrared wavelength and the second infrared wavelength. It must be noted that the wide-responsive infrared sensor 73 is also provided in a further example in relation with the other features shown in FIG. 3A. Still further, also the first and second infrared sensors 69, 71, as shown in FIG. 3A, are provided in a further example, not shown, in relation with the other features of FIG. 3C (described further below).

FIG. 3B shows a further example, where a first infrared emitter 70 and a second infrared emitter 72 are provided. The first infrared emitter is providing a first spectrum comprising the first infrared wavelength, as indicated with arrow 66, and the second infrared emitter is providing a second spectrum comprising the second infrared wavelength, as indicated with arrow 68.

FIG. 3C shows a further example, where, as the infrared sensor device 63, the sensor arrangement 24 comprises the wide-responsive infrared sensor 73, as mentioned above.

It must be noted that the emitter solutions of FIGS. 3A, 3B, and FIG. 3C are provided as alternative options.

The wide spectrum radiation of FIG. 3A is also referred to as dual radiation spectrum.

Figure 3D:
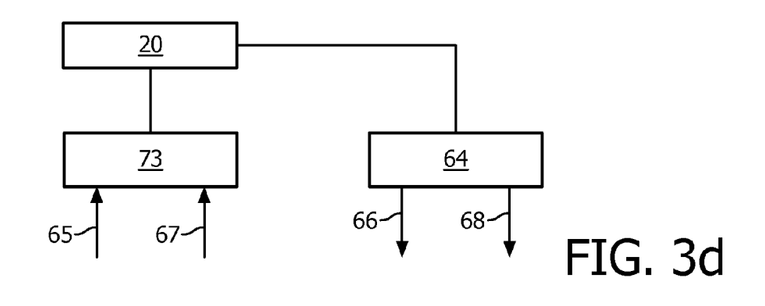
FIG. 3D shows a fourth example.

FIG. 3D shows an example of the apparatus 10 where the wide-responsive infrared sensor 73 is provided in combination with the bi-functional light source 64.

It must be noted that the arrangement of the emitter arrangement 22 and the sensor arrangement 24, and the respectively shown sensors and emitters are shown in a schematic arrangement for illustrational purposes. Of course, different spatial arrangements in relation to each other and in relation to the food inside the container 12 are provided.

According to a further example, the emitter arrangement 22 is configured to emit the first or second sensing radiation as a visible sensing radiation, and the second or first sensing radiation as an infrared sensing radiation. For example, the sensor arrangement 24 comprises a first visible light sensor 76 to detect light with the first or second visible wavelength. Further, a first infrared light sensor 78 is provided to detect light with the first or second infrared wavelength.

Figure 4A:
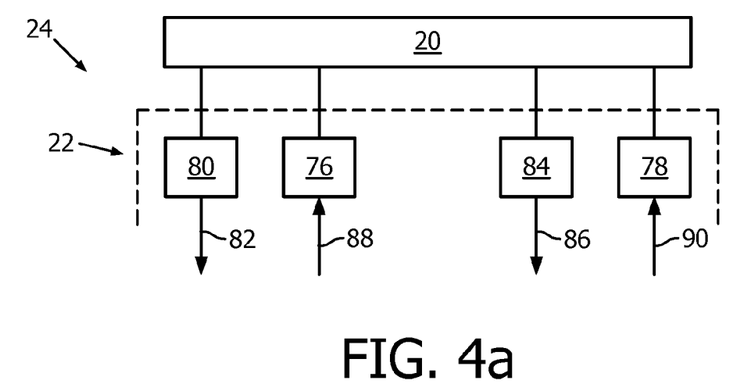
FIG. 4A shows a first example of a still further example with a mixed sensing radiation, FIG. 4B a second example, and FIG. 4C a third example.

FIG. 4A shows an example, where the emitter arrangement 22 comprises a first visible light emitter 80 providing a visible light spectrum with a first sensing peak wavelength in the visible light wavelength range, as indicated with arrow 82. Further, the emitter arrangement 22 comprises a first infrared light emitter 84 providing an infrared spectrum with a second sensing peak wavelength in the infrared wavelength range, as indicated with arrow 86.

A first reflection arrow 88 indicates the reflected light with the first or second visible wavelength, and a second reflection arrow 90 indicates the reflected light with the first or second infrared wavelength.

Figure 4B:
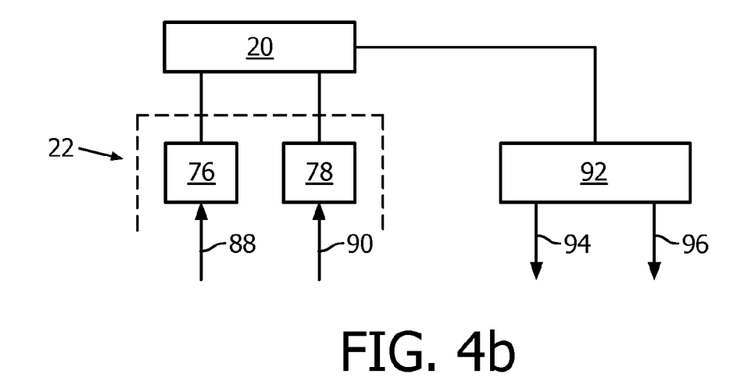

FIG. 4B shows a further example, where, as the emitter arrangement 22, one of the at least one heating radiation sources is provided as a bi-functional radiation source $LS_{BI-F}$, indicated with reference numeral 92, configured to emit light for measuring purposes with a wide spectrum radiation comprising the visible sensing radiation, as indicated with reference numeral 94, and the infrared sensing radiation, as indicated with reference numeral 96.

Figure 4C:
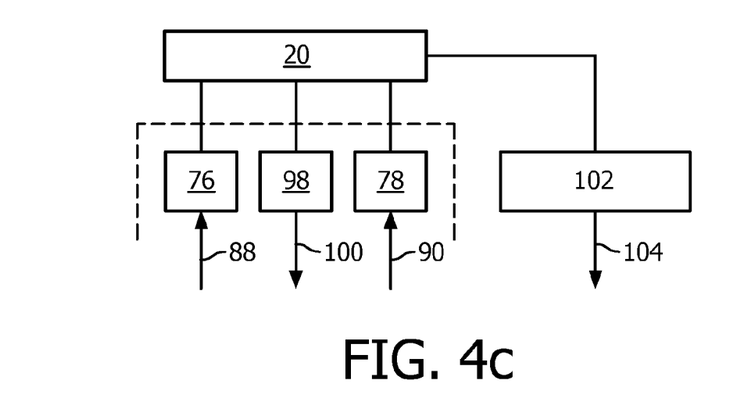

FIG. 4C shows an example, wherein the emitter arrangement 22 comprises an emitter 98 providing the infrared sensing radiation or the visible sensing radiation, which two options are indicated with arrow 100, and one of the at least one heating radiation sources is provided as a bi-functional light source $LS_{BI-F}$, indicated with reference numeral 102, configured to emit light for measuring purposes with a wide spectrum radiation comprising the visible sensing radiation; or a radiation spectrum comprising the infrared sensing radiation, which two options are indicated with arrow 104.

In a further example, the emitter arrangement 22 is configured to emit one of the sensing radiations as visible sensing radiation $SRA_{VIS}$ with a visible wavelength $SWL_{VIS}$, and one of the sensing radiations as infrared sensing radiation $SRA_{IR}$ with an infrared wavelength $SWL_{IR}$.

In an example, as an infrared sensor, one of the heating sources is provided as discussed above.

The wide spectrum radiation of FIGS. 4B and 4C is also referred to as dual radiation spectrum.

According to a further example, the emitter arrangement 22 is configured to emit light as third sensing radiation $SRA_3$ with a third sensing peak wavelength $SWL_3$.

Figure 5A:
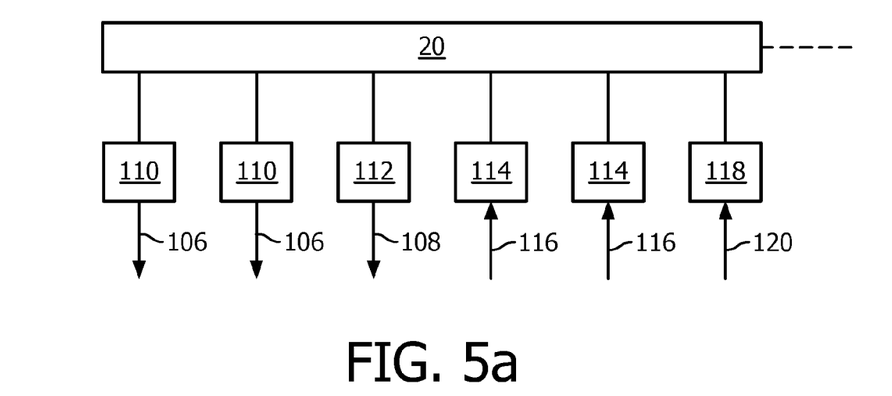
FIG. 5A shows a first example of a still further example of a mixed sensing radiation application, FIG. 5B a second example, and FIG. 5C a third example.

FIG. 5A shows an example where two sensing radiations are provided as visible sensing radiations with visible wavelengths, the two sensing radiations indicated with reference numeral 106. A third sensing radiation 108 is provided as infrared sensing radiation with an infrared wavelength. Two visible light emitters 110 and one infrared emitter 112 are provided. Further, two visible light sensors 114 are provided to detect reflected visible light 116. Still further, one infrared sensor 118 is provided to detect reflected infrared light 120.

Figure 5B:
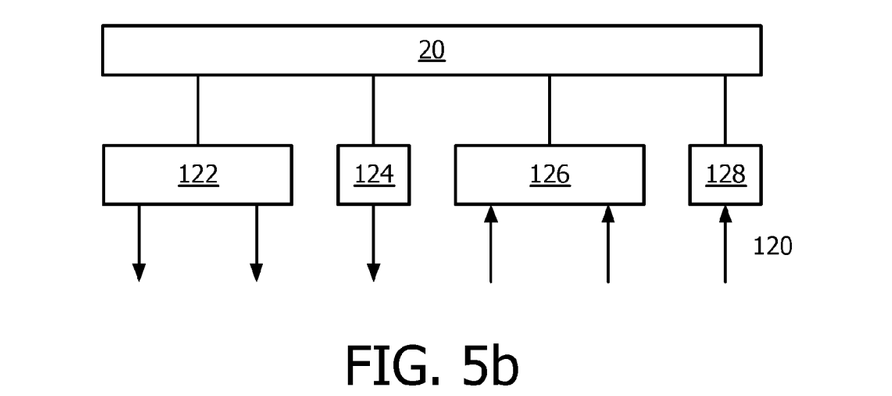

In a further example, two sensing radiations are provided as infrared sensing radiations with infrared wavelengths, and a third sensing radiation is provided as visible sensing radiation with a visible wavelength. An infrared emitter device providing the first spectrum comprising the first infrared wavelength and the second spectrum comprising the second infrared wavelength is provided, and one visible light emitter.

The emitter device has reference numeral 122, and the visible light emitter has reference numeral 124.

Further, an infrared sensor device 126 to detect light with the first and the second infrared wavelength is provided, and one visible light sensor 128.

In a further example of FIG. 5B, the infrared emitter device 122 is provided as a bi-functional light source configured to emit light for measuring purposes with a wide spectrum radiation comprising the first infrared wavelength and the second infrared wavelength. This is indicated in FIG. 5B with the common frame at reference numeral 122.

In a further example of FIG. 5B, although not further shown, the infrared emitter device is provided as two infrared light emitters. The first emitter is providing the first spectrum comprising the first infrared wavelength, and the second emitter is providing the second spectrum comprising the second infrared wavelength.

Figure 5C:
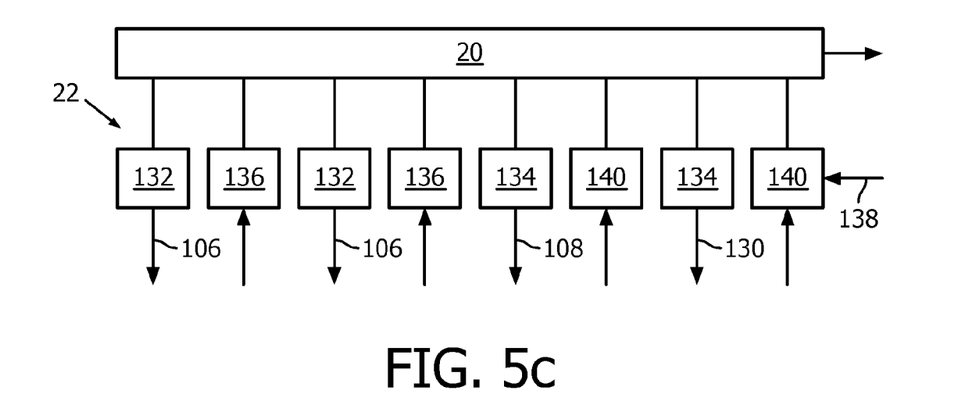

FIG. 5C shows a further example, where the emitter arrangement 22 is further configured to emit light as fourth sensing radiation $SRA_4$ with a fourth sensing peak wavelength $SWL_4$. The fourth light is indicated with reference numeral 130. Two sensing radiations are provided as visible sensing radiations with visible wavelengths, and two sensing radiations are provided as infrared sensing radiations with infrared wavelengths. Two visible light emitters 132 and two infrared emitters 134 are provided. Still further, two visible light sensors 136 and an infrared sensor device 138 is provided to detect light with the first infrared wavelength and light with the second infrared wavelength.

In an example, as the infrared sensor device 138, the sensor arrangement comprises a first infrared sensor to detect light with a first infrared wavelength and a second infrared sensor to detect light with a second infrared wavelength, as indicated with reference numeral 140 for the two infrared sensors in FIG. 5C.

In a further example, not further shown, as the infrared sensor device 138, a wide-responsive infrared sensor with a plateau-shaped responsive curve covering the first infrared wavelength and the second infrared wavelength is provided.

According to an example, the first visible wavelength of the first visible sensing radiation is approximately 550 nm. The second visible wavelength of the second visible sensing radiation is approximately 780 nm.

According to a further example, the first infrared wavelength of the first infrared sensing radiation is approximately 1200 nm. The second infrared wavelength of the second infrared sensing radiation is approximately 1300 nm.

It must be noted that the given wavelengths are provided for all of the above-mentioned different combinations.

The heating module 18 provides the first heating peak wavelength and the second heating peak wavelength in an example in the infrared wavelength range. The first heating peak wavelength is approximately 1.200 nm, and the second heating peak wavelength is approximately 1.600 nm.

Figure 6A:
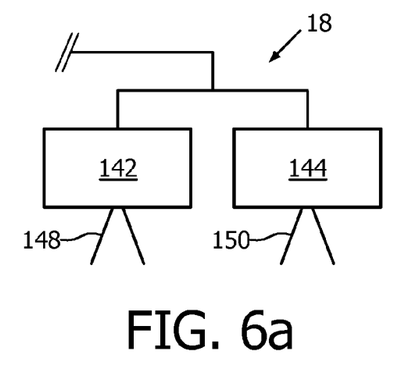
FIG. 6A shows a first example of a heating module, and FIG. 6B a second example.

FIG. 6A shows an example, where the heating module 18 comprises a first heating lamp 142 and a second heating lamp 144. The first heating lamp 142 is configured to provide first light radiation portion 148 with the first heating peak wavelength, and the second heating lamp 144 is configured to provide second light radiation portion 150 with the second heating peak wavelength.

Figure 6B:
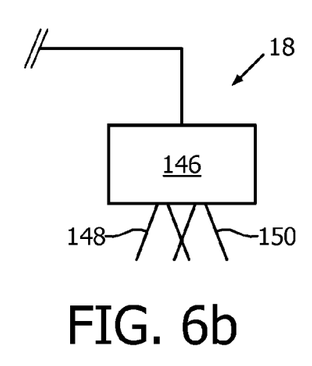

FIG. 6B shows an example, where the heating module 18 comprises a spectrally adaptable heating lamp 146, configured to provide an adaptable radiation spectrum comprising a first light radiation portion with the first heating peak wavelength, and a second light radiation portion with the second heating peak wavelength. The ratio of the first light radiation portion and the second light radiation portion is adaptable.

With reference to FIG. 1A in particular, it must be noted that, in a further example, a plurality of the first and the second emitters is provided. For example, the emitters and the sensors are mounted at an inner ceiling of the container (not further shown) with the emitters and the sensors facing towards the volume.

According to a further example, the heaters are mounted at an inner ceiling of the container with the emitters and the sensors facing towards the volume, but below the emitters and sensors, and without overlapping with emitters and sensors.

For example, a round container is provided and a number of light sources and sensors is provided in a distributed manner, for example in a circular fashion, on a respectively circular lid or cover on the inside facing towards the food.

With reference to FIG. 1, it is noted that according to an example, the apparatus 10 is a desk-appliance apparatus.

The term "desk-appliance" refers to an apparatus that is suitable for household purposes, which apparatus can be placed on different working surfaces of a table in a kitchen, or can be placed in a shelf or on a cupboard. The desk-appliance relates to an appliance that can be manually moved and carried to different places by a single person. For household purposes, the volume occupied by the appliance is constrained to sizes as small as possible. In an example, the desk-appliance relates to a portable appliance.

It must be noted that when referring to one of the group of first visible light sensor, and second visible light sensor, first visible light emitter, and second visible light emitter, bi-functional light source, infrared sensor device, first infrared emitter, and second infrared emitter, and wide-responsive infrared sensor, it is provided at least one of these, i.e. it is provided to have one, two, three, or also more than three of these, for example five or ten of the respective type. This is also the case for the mixed arrangement, where it is provided to have one or more than one of the respective kind/type of emitters and detectors.

Figure 7:
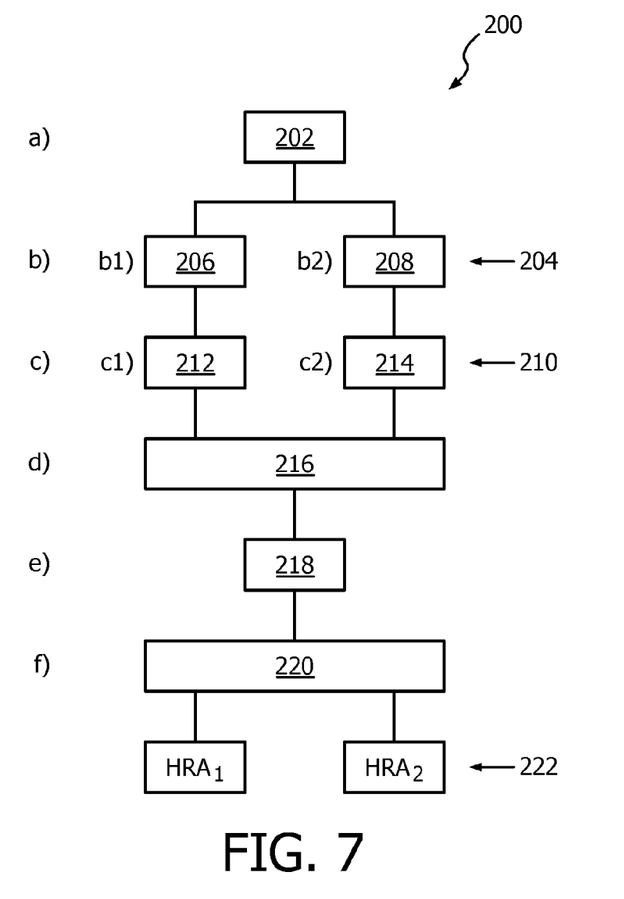
FIG. 7 shows basic steps of an example of a method for reheating cooked food.

FIG. 7 shows a method 200 for reheating cooked food, comprising the following steps:

In a first step 202, cooked food to be reheated is arranged in a container.

In a second step 204, radiation is emitted to the food. It is provided a first sub-step 206, in which a first sensing radiation with a first sensing peak wavelength is emitted, and a second sub-step 208, in which a second sensing radiation with a second sensing peak wavelength is emitted. The first and the second sensing radiations have different reflecting characteristics in relation with fat and protein in the food, e.g. meat to be reheated.

In a third step 210, light that is reflected by the food is detected. It is provided a first sub-step 212, in which light with the first sensing peak wavelength is detected, and a second sub-step 214, in which light with the second sensing peak wavelength is detected.

In a fourth step 216, a fat/protein ratio of the food arranged in the container based on the light detected in sub-steps 212 and 214 is determined.

In a fifth step 218, operating parameters for a heating module, e.g. for an optimal reheating procedure, are determined.

In a sixth step 220, the heating radiation source is controlled such that light as first heating radiation $HRA_1$ with a first heating peak wavelength $HWL_1$, and light as second heating radiation $HRA_2$ with a second heating peak wavelength $HWL_2$ is emitted 222 to the food in the container thereby reheating the cooked food. A power output of the first heating peak wavelength and the second heating peak wavelength is adapted to have a different absorption characteristics relating to fat and protein of the food, e.g. meat.

The first step 202 is also referred to as step a), the second step 204 as step b), with the first sub-step 206 as sub-step b1), and the second sub-step 208 as sub-step b2), the third step 210 as step c), with the first sub-step c1) for the sub-step 212, and sub-step c2) for the sub-step 214, the fourth step 216 as step d), the fifth step 218 as step e), and the sixth step 220 as step f).

It is noted that the emitting steps and detecting steps are basically performed at the same time, or at least in a very fast sequence, since in the detecting step light is detected that has been emitted in the emitting step and that has been reflected by the food/meat.

In an example, the steps b) and c) are provided such that the two emitting sub-steps b1) and b2) are performed simultaneously, and the two detecting (or sensing) sub-steps c1) and c2) are performed simultaneously.

In a further example, the steps b) and c) are provided interleaved such that the first emitting sub-step b1) and the first detecting (or sensing) sub-step c1) are performed first, and the second emitting sub-step b2) and second detecting (or sensing) sub-step c2) are performed afterwards.

In the following, a further example of determining a fat/protein ratio and the respective cooking procedure is provided. Besides water, cooked meat mainly contains protein and fat. The content of protein and fat are different among different types of meat (e.g., pork, beef, lamb, etc). For one type of meat, the content of protein and fat are also different depending on from which part of the animal meat is cut. Therefore an estimation of the fat/protein ratio is a parameter for a good heating of meat. Being radiated by VIS and IR light (wavelength range 500 nm to 2000 nm), protein and fat in cooked meat will show different light reflection property (not further shown in the figures). As can be observed in the VIS spectrum, fat has a relatively stable reflection rate to lights of wavelength from 500 nm to 800 nm, while protein has a big change on the reflection of lights of wavelength 550 nm and 780 nm. For example:

For fat: $(R_{780}-R_{550})/R_{550}=(64.7\%-54.2\%)/54.2\%=19\%$

For protein: $(R_{780}-R_{550})/R_{550}=(69.3\%-38.5\%)/38.5\%=80\%$

As can be observed in the IR spectrum, protein has a very similar reflection rate to lights of wavelength from 1200 nm to 1300 nm, while fat has a big difference on the reflection of lights of wavelength 1200 and 1300 nm. For example:

For fat: $(R_{1300}-R_{1200})/R_{1200}=(43.5\%-20.9\%)/20.9\%=108\%$

For protein: $(R_{1300}-R_{1200})/R_{1200}=(37.7\%-37.9\%)/37.9\%=\sim 0\%$

Such difference between fat and protein on the reflection of lights with the two VIS wavelengths (550 nm/780 nm) and the two IR wavelengths (1200 nm/1300 nm) are used to estimate the fat/protein ratio of cooked meat.

Being radiated by IR light (wavelength range 800 nm to 2000 nm), protein and fat in cooked meat will show different light absorption property. The absorbed light heats the meat. The higher the absorption rate, the more the energy of the heating source is used for heating. For energy efficiency, the absorption rate should not below 50%. As can be observed, fat absorbs roughly the same amount of energy from light with wavelength 1200 nm and light with wavelength 1600 nm, while protein absorbs more energy from light with wavelength 1600 nm than light with wavelength 1200. For example:

For 1200 nm: $(A_{fat}-A_{protein})/A_{protein}(73.3\%-57.3\%)/57.3\%=28\%$

For 1600 nm: $(A_{protein}-A_{fat})/A_{fat}=(87.2\%-68.0\%)/68.0\%=28\%$

For fat: $(A_{1200\ nm}-A_{1600\ nm})-(73.3\%-68.0\%)-5\%$

For protein: $(A_{1600\ nm}-A_{1200\ nm})=(87.2\%-57.3\%)=30\%$

These differences between fat and protein on the absorption of lights with the two IR wavelengths (1200 nm/1600 nm) is used to adjust the power output of the two infrared heaters matching the estimated fat/protein ratio so as to deliver a better reheating result.

The measurement of the fat/protein ratio is now illustrated by using VIS emitters/sensors as the example:

The emitters with peak wavelength at 550 nm radiate the meat with a predetermined optical power (P1). In the meantime the sensors with response peak at 550 nm start measuring the amount of light reflected by the meat. The average of the measured value of all the sensors is recorded as A. Then the emitters stop radiation. This step takes several seconds.

The emitters with peak wavelength at 780 nm radiate the meat with a predetermined optical power (P2). In the meantime the sensors with response peak at 780 nm start measuring the amount of light reflected by the meat. The average of the measured value of all the sensors is recorded as B. Then the emitters stop radiation. This step takes several seconds. To simplify, it is assumed P1=P2. The value of (B−A)/A is used to estimate the fat/protein ratio. The value is in between 20% (all fat) and 80% (all protein). Through pre-measurements a formula can be established to calculate the rough fat/protein ratio by this value. In case P1 is not equal to P2, the value of (P1−P2) must be considered when establish the formula. In a similar way, the measurement can be done by using IR emitters/sensors.

To reheat the meat:

Fat/protein ratio is low (1:15 to 1:8): only the infrared heater with peak wavelength at 1600 nm is turned on to heat the meat. This way more energy is used to heat protein than fat. It is not necessary to turn on the infrared heater with peak wavelength at 1200 nm since fat will have a similar absorption rate to 1200 nm and protein will have a lower absorption rate to 1200 nm.

Fat/protein ratio is high (e.g., 1:8 to 1:1): the infrared heater with peak wavelength at 1200 nm is turned on to heat the meat. This way, more energy is used to heat fat than protein. Since protein has a lower absorption rate to 1200 nm wavelength, the infrared heater with peak wavelength at 1600 nm can work in a pulse mode if the meat contains more protein than fat. The duty cycle of the 1600 nm heater is adjusted according to the fat/protein ratio: the more the protein, the higher the duty cycle.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. Apparatus for reheating cooked food, comprising:
   a container for receiving food to be reheated;
   a sensing module;
   a heating module; and
   a processing unit;
   wherein the sensing module is provided with:
   an emitter arrangement configured to emit at least:
   light as first sensing radiation ($SRA_1$) with a first sensing peak wavelength ($SWL_1$), and light as second sensing radiation ($SRA_2$) with a second sensing peak wavelength ($SWL_2$);
wherein the first and the second sensing radiations have different reflecting characteristics in relation with fat and protein in the food to be reheated; and
  a sensor arrangement configured to detect light with the first sensing peak wavelength and light with the second sensing peak wavelength; wherein the light is reflected by the food; and
  wherein the heating module is configured to provide energy to the food arranged in the container by at least one heating radiation source for heating the food in dependency of a determined fat/protein ratio;
  wherein the processing unit is configured to determine the fat/protein ratio of the food arranged in the container based on the detected light reflected by the food;
  wherein the processing unit is configured to determine operating parameters of the heating module; and
  wherein the processing unit is configured to control the heating radiation source to emit:
    light as first heating radiation ($HRA_1$) with a first heating peak wavelength ($HWL_1$), and
    light as second heating radiation ($HRA_2$) with a second heating peak wavelength ($HWL_2$);
wherein a power output of the first heating peak wavelength and the second heating peak wavelength is adapted to have a different absorption characteristics relating to fat and protein of the food.

2. Apparatus according to claim 1, wherein the processing unit is configured to determine operating parameters of the heating module for a reheating procedure such that fat parts and protein parts are equally heated.

3. Apparatus according to claim 1, wherein the emitter arrangement is configured to emit:
  the first sensing radiation as a first visible sensing radiation ($SRA_{VIS1}$) with a first visible wavelength ($SWL_{VIS1}$); and
  the second sensing radiation as a second visible sensing radiation ($SRA_{VIS2}$) with a second visible wavelength ($SWL_{VIS2}$);
    wherein, the sensor arrangement comprises:
    a first visible light sensor to detect light with the first visible wavelength, and
    a second visible light sensor to detect light with the second visible wavelength; and
    wherein one of the following is provided:
i1) a first and a second visible light emitter are provided; wherein:
  the first visible light emitter is providing a first spectrum comprising the first visible wavelength; and
  the second visible light emitter is providing a second spectrum comprising the second visible wavelength; or
i2) the emitter arrangement is provided with a wide-spectrum-emitter providing a wide spectrum radiation comprising the first visible wavelength and the second visible wavelength; or
i3) as the emitter arrangement, one of the at least one heating radiation sources is provided as a bi-functional light source configured to emit light for measuring purposes with a wide spectrum radiation comprising the first visible wavelength and the second visible wavelength.

4. Apparatus according to claim 3, wherein:
  the first visible wavelength of the first visible sensing radiation is approximately 550 nm, and
  the second visible wavelength of the second visible sensing radiation is approximately 780 nm.

5. Apparatus according to claim 1, wherein the emitter arrangement is configured to emit:
  the first sensing radiation as a first infrared sensing radiation ($SRA_{IR1}$) with a first infrared wavelength ($SWL_{IR1}$); and
  the second sensing radiation as a second infrared sensing radiation ($SRA_{IR2}$) with a second infrared wavelength ($SWL_{IR2}$);
    wherein, the sensor arrangement comprises:
    an infrared sensor devices to detect light with the first infrared wavelength, and to detect light with the second infrared wavelength; and
    wherein one of the following is provided:
ii1) wherein as the emitter arrangement, one of the at least one heating radiation sources is provided as a bi-functional light source configured to emit light for measuring purposes with a wide spectrum radiation comprising the first infrared wavelength and the second infrared wavelength; or
ii2) a first and a second infrared emitter are provided; wherein:
  the first infrared emitter is providing a first spectrum comprising the first infrared wavelength; and
  the second infrared emitter is providing a second spectrum comprising the second infrared wavelength.

6. Apparatus according to claim 5, wherein, as the infrared sensor device, the sensor arrangement comprises:
  a first infrared sensor to detect light with the first infrared wavelength, and a second infrared sensor to detect light with the second infrared wavelength; or
  a wide-responsive infrared sensor with a plateau-shaped responsive curve covering the first infrared wavelength and the second infrared wavelength.

7. Apparatus according to claim 5, wherein:
  the first infrared wavelength of the first infrared sensing radiation is approximately 1200 nm, and
  the second infrared wavelength of the second infrared sensing radiation is approximately 1300 nm.

8. Apparatus according to claim 1, wherein the emitter arrangement is configured to emit:
  the first or second sensing radiation as a visible sensing radiation; and
  the second or first sensing radiation as an infrared sensing radiation; and
    wherein, the sensor arrangement comprises:
    a first visible light sensor to detect light with the first or second visible wavelength, and
    a first infrared light sensor to detect light with the first or second infrared wavelength; and
    wherein one of the following is provided:
iii1) the emitter arrangement comprises:
  a first visible light emitter providing a visible light spectrum with a first sensing peak wavelength in the visible light wavelength range; and
  a first infrared light emitter providing an infrared spectrum with a second sensing peak wavelength in the infrared wavelength range; or
iii2) as the emitter arrangement, one of the at least one heating radiation sources is provided as a bi-functional light source configured to emit light for measuring purposes with a wide spectrum radiation comprising the visible sensing radiation and the infrared sensing radiation; or
iii3) the emitter arrangement comprises an emitter providing the infrared sensing radiation or the visible sensing radiation; and one of the at least one heating radiation sources is provided as a bi-functional light source configured to emit light for measuring purposes with:
  a wide spectrum radiation comprising the visible sensing radiation; or
  a radiation spectrum comprising the infrared sensing radiation.

9. Apparatus according to claim wherein the emitter arrangement is configured to emit:
light as third sensing radiation ($SRA_3$) with a third sensing peak wavelength ($SWL_3$);
wherein one of the following is provided:
iv1) two sensing radiations are provided as visible sensing radiations with visible wavelengths, and a third sensing radiation is provided as infrared sensing radiation with an infrared wavelength; wherein two visible light emitters and one infrared emitter are provided; and wherein two visible light sensors and one infrared sensor are provided; or
iv2) two sensing radiations are provided as infrared sensing radiations with infrared wavelengths, and a third sensing radiation is provided as visible sensing radiation with a visible wavelength; wherein an infrared emitter device providing the first spectrum comprising the first infrared wavelength and the second spectrum comprising the second infrared wavelength, and one visible light emitter are provided; and wherein an infrared sensor device to detect light with the first and the second infrared wavelength and one visible light sensor are provided; or
iv3) wherein the emitter arrangement is further configured to emit:
light as fourth sensing radiation ($SRA_4$) with a fourth sensing peak wavelength ($SWL_4$); and
wherein two sensing radiations are provided as visible sensing radiations with visible wavelengths, and two sensing radiations are provided as infrared sensing radiations with infrared wavelengths; and wherein two visible light emitters and two infrared emitters are provided; and wherein two visible light sensors and an infrared sensor device to detect light with the first infrared wavelength and light with the second infrared wavelength are provided.

10. Apparatus according to claim 1, wherein the first heating peak wavelength and the second heating peak wavelength are in the infrared wavelength range; and
wherein the first heating peak wavelength is approximately 1200 nm, and the second heating peak wavelength is approximately 1600 nm.

11. Apparatus according to claim 1, wherein the heaters are mounted at an inner ceiling of the container with the emitters and the sensors facing towards the volume, but below the emitters and sensors and without overlapping with emitters and sensors.

12. Apparatus according to claim 1, wherein the heating module comprises a first heating lamp and a second heating lamp; and
wherein first heating lamp is configured to provide first light radiation with the first heating peak wavelength and the second heating lamp is configured to provide second light radiation with the second heating peak wavelength.

13. Apparatus according to claim 1, wherein the heating module comprises a spectrally-adaptable heating lamp configured to provide an adaptable radiation spectrum comprising:
a first light radiation portion with the first heating peak wavelength, and
a second light radiation portion with the second heating peak wavelength; and
wherein the ratio of the first light radiation portion and the second light radiation portion is adaptable.

14. Apparatus according to claim 1, wherein the apparatus is a desk-appliance apparatus.

15. A method for reheating food, comprising the following steps:
wherein the sensing module is configured to measure a fat/protein ratio of food arranged in the container; and wherein the sensing module is provided with:
a) arranging cooked food to be reheated in a container;
b) emitting radiation to the food; wherein it is provided:
   b1) emitting a first sensing radiation with a first sensing peak wavelength, and
   b2) emitting a second sensing radiation with a second sensing peak wavelength;
   wherein the first and the second sensing radiations have different reflecting characteristics in relation with fat and protein in the food to be reheated;
c) detecting light reflected by the food; wherein it is provided:
   c1) detecting light with the first sensing peak wavelength; and
   c2) detecting light with the second sensing peak wavelength;
d) determining a fat/protein ratio of the food arranged in the container based on the light detected in sub-steps c1) and c2);
e) determining operating parameters for a heating module; and
f) controlling the heating radiation source such that:
   light as first heating radiation ($HRA_1$) with a first heating peak wavelength ($HWL_1$), and
   light as second heating radiation ($HRA_2$) with a second heating peak wavelength ($HWL_2$) is emitted to the food in the container thereby reheating the cooked food;
   wherein a power output of the first heating peak wavelength and the second heating peak wavelength is adapted to have a different absorption characteristics relating to fat and protein of the food.

* * * * *